United States Patent [19]

Sengebusch et al.

[11] 4,364,113

[45] Dec. 14, 1982

[54] CRACK DEVELOPMENT MEASURING EQUIPMENT

[75] Inventors: Peter Sengebusch, Bergisch Gladbach; Horst Nowack, Wetter, both of Fed. Rep. of Germany

[73] Assignee: Deutsche Forschungs- und Versuchsanstalt fur Luft- und Raumfahrt e.V., Cologne, Fed. Rep. of Germany

[21] Appl. No.: 179,519

[22] Filed: Aug. 19, 1980

[30] Foreign Application Priority Data

Aug. 23, 1979 [DE] Fed. Rep. of Germany ....... 2934038

[51] Int. Cl.³ .............................................. H04N 7/18
[52] U.S. Cl. .................. 364/507; 358/105; 358/106
[58] Field of Search ............ 364/507, 525, 514; 358/105, 106, 108

[56] References Cited

U.S. PATENT DOCUMENTS

| | | | |
|---|---|---|---|
| 4,063,282 | 12/1977 | Exton | 358/106 |
| 4,136,950 | 1/1979 | Labrum et al. | 358/105 X |
| 4,163,991 | 8/1979 | Burrig | 358/106 X |
| 4,185,298 | 1/1980 | Billet et al. | 358/106 |
| 4,219,847 | 8/1980 | Pinkney et al. | 358/105 X |
| 4,240,109 | 12/1980 | Michael et al. | 358/105 |
| 4,245,243 | 1/1981 | Gutjahr et al. | 358/106 |
| 4,249,212 | 2/1981 | Ito et al. | 358/105 X |

*Primary Examiner*—Edward J. Wise

[57] ABSTRACT

The measuring equipment is used for the optical monitoring of cracks in material test pieces, which are loaded by a loading device. A television camera trained on the test piece is connected to a discriminator which converts the image points of the television image into binary pulses. The binary pulses of the television image are stored from time to time in a store. A comparator compares the contents of the store with the binary pulses of a consecutive television image and ascertains deviations between two consecutively-taken television images. The number of the non-coincident binary pulses of the compared television images is counted and indicated.

17 Claims, 1 Drawing Figure

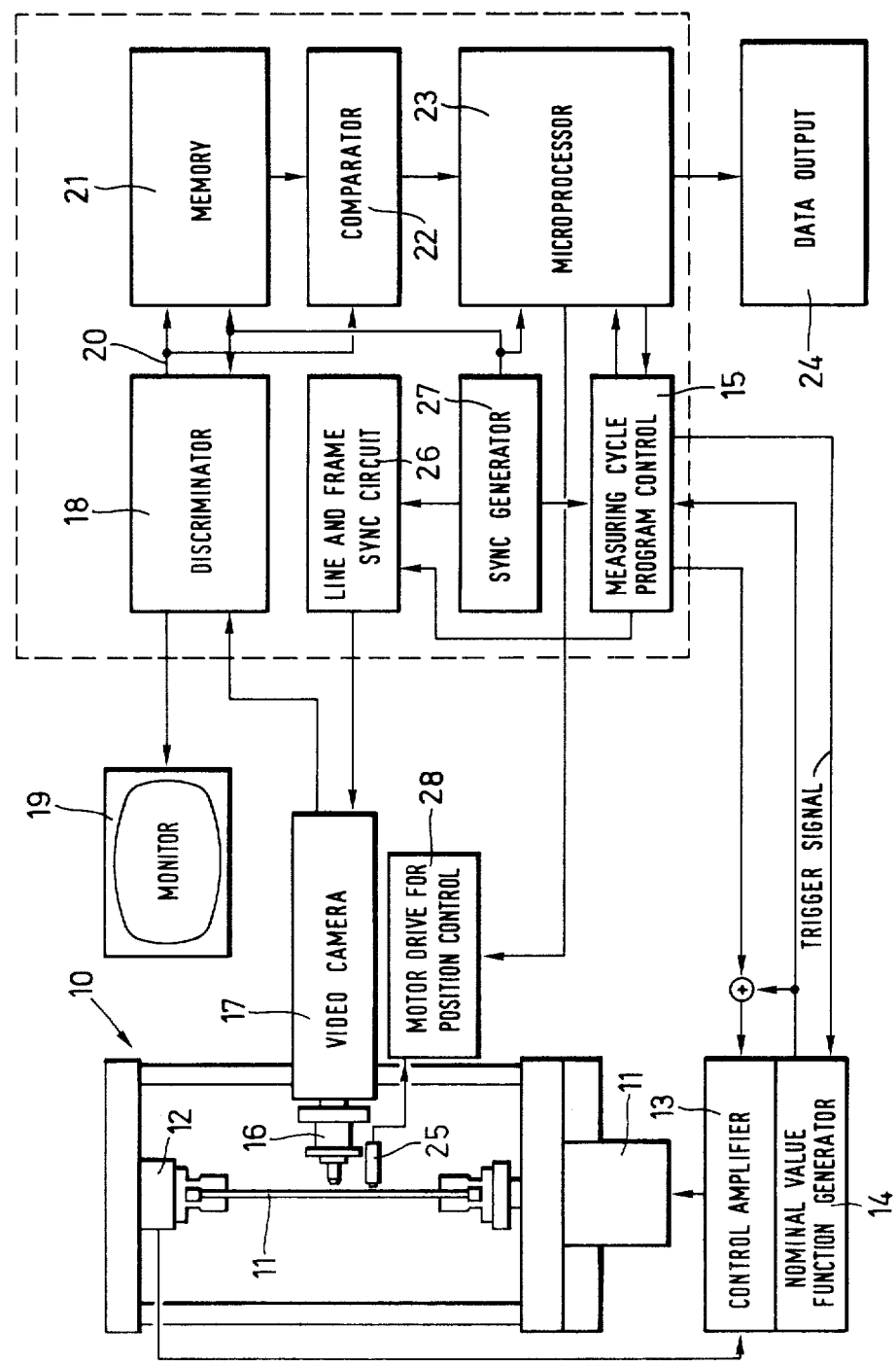

CRACK DEVELOPMENT MEASURING EQUIPMENT

The invention relates to crack development measuring equipment with a loading device in which a test piece can be clamped, and an optical measuring tool trained on the test piece.

In the inspection of material of test pieces, the length of cracks has frequently to be determined and the development of the crack to be measured during static or vibratory stressing of the test piece. The crack length is ascertained with a microscope and measured at fixed intervals or, in the case of vibratory stressing, after a fixed number of stress cycles. This conventional method of measurement requires a considerable amount of time for each individual measurement and favours the origination of errors of measurement.

The problem of the invention is to provide crack development measuring equipment of the kind mentioned at the beginning which makes possible the measurement at the time being considered of material cracks along the test piece objectively and with great precision, and moreover operates at very high speed, so that the individual measurements are already available a short time afterwards and can, if necessary, be processed electronically.

For the solution of this problem, provision is made in accordance with the invention for the optical measuring tool to have a television camera which is connected to a discriminator which converts the image points of the television image into binary pulses, for the discriminator to be connected to a store taking up the binary pulses of a television image and for a comparator to be provided which compares the contents of the store with the binary pulses of a consecutive television image.

The television camera monitors the material test piece surface and thus first of all produces a series of analogue video signals as well as the required sync signals. Video signals and sync signals are separated in the discriminator and the video signal digitized. The digital (binary) video signals are stored in the store in the form of lines and dots. The store is of sufficient capacity to store a pulse for each image point of the television image. The storing of a television image occurs once at the start of the test and every time a crack measurement is to take place during the course of the test.

The video signal occurring at each crack measurement is supplied to one input of the comparator, the second input of which is connected with the output of the store. A comparison then takes place in the comparator between the contents of the image storing locations and the corresponding instantaneous value of the video signal and the new image is filed in the image store. If no variations appear at the comparison, a NOT-pulse is issued. If, on the contrary, variations appear between the contents of the store and the additional television image monitored at a freely-selectable point of time, a YES-pulse is issued, i.e. a spreading of the fatigue crack has taken place. In this way it can be ascertained very quickly and reliably whether a crack has formed since the last measurement or whether a crack already existing has spread.

If there are on the test piece surface disturbing optical phenomena, e.g. scratches, which are detected by the television camera but do not represent a crack, then these are not analyzed by the crack development measuring equipment and on the whole not sensed by the comparator, as they are identically contained in the television image present in the store and also in the television image later monitored. The crack development measurement relies on the recognition of the sides of the crack (outline of the crack), which reflect the light of the test-piece illumination differently from the crack surroundings. Although various gray tints besides dark and light appear in the television image, depending on reflection, angle and intensity of the light, a binary conversion in pure black and white is undertaken, as the gray tints are not of interest.

In order to obtain quantitative evidence concerning the development of the crack, in a practical further development of the invention, the number of non-coincident binary pulses of the compared television images is counted and indicated. There is obtained therewith, within the shortest time, reliable numerical data concerning the enlargement of the crack since the point of time of the last measurement.

To achieve a high resolution of the television image for the analyzing of the finest cracks, a front microscope attachment is connected to the television camera. In this way, for example with 100-fold magnification and a size of area of measurement of $300\mu$ a resolution of $2.5\mu$ can be obtained when the television image has 120 lines, or a resolution of $1.25\mu$ when the television image has 240 lines.

Advantageously the line direction of the television camera is at right angles to the direction of the crack and the comparison of the television images takes place through linear comparisons. The crack extension may also be quantitatively determined by the number of lines in which a change in the picture content has taken place compared with the last analysis. These lines can be counted.

Advantageously the television camera is mounted on a sliding carriage which can be moved under control in three planes passing at right angles to one another. The control of the sliding carriage may ensue as a function of the measured crack enlargement. In that way it is ensured that there always appears in the television image that part of the test piece which is of interest for the measurement or in which the crack enlargement takes place. If, for example the crack approaches the left-hand edge of the television image, the camera is moved a definite amount to the right. If the crack expands during the course of the test, there is a following movement of the camera in the crack expansion direction by a definite amount, exactly parallel to the test piece. The range of the depth of focus is kept constant with the help of a receiver.

The loading of the crack development test piece is controlled in such a way that the loading of the test piece is at a standstill for a short time during the taking of the additional television image. In this way it is ensured that the measurements are not falsified through oscillatory movements of the test piece. As the measurement requires only a very short time (maximum 40 ms), only a very short stoppage is necessary for the measurement.

An exemplary embodiment of the invention is described hereinafter in more detail with reference to the single FIGURE of the drawing.

In the drawing there is represented a simplified block diagram of the crack development measuring equipment. A test piece 11 is clamped vertically in the loading device denoted 10. The loading device 10 has at its lower end a test cylinder 11 which produces tensile, compressive or vibratory loads along the test piece. A device 12 for measurement of the load is mounted at the upper holder of the test piece. The pressure gauge 12 is connected with one input of a variable-gain amplifier 13, the output signal from which controls the valve of the test cylinder 11. At the other input of the control amplifier 13 are the output signal of a function generator 14 for the nominal value as well as the control signal of the measuring cycle program control 15.

The front microscope attachment 16 of the television camera 17 is directed on to a part of the surface of the test piece 11. The television camera 17 thus takes an image of the respective part of the test piece 11 and supplies this together with the sync signals to the discriminator 18. The discriminator 18 delivers the image and sync signals to a monitor 19 at which the input television image is made visible. Moreover, the discriminator 18 contains a device for producing a reference grid on the monitor 19. This reference grid, which consists of horizontal and vertical strips, facilitates the adjustment of the television camera with reference to the test piece surface zone to be accommodated.

The discriminator 18 moreover separates the image pulses from the sync pulses of the television camera 17 and digitizes the image pulses with the help of a threshold circuit, so that in the case of the image pulses discrimination is between black and white only. These binary image pulses, which occur at the output 20 of the discriminator 18, are supplied to the store 21 and the comparator 22. The store, in the case of 120 units of measurement, has a minimum storage capacity of 10K and is therewith capable of holding all image points of the television image.

The store thus retains the television image last taken. In the comparator 22 the television image contained in the store 21 is compared with the next following television image in order to ascertain whether or not the two television images are identical. As the line direction of the television camera 17 is oriented at right angles to the orientation of a crack along the test piece, the comparison of the two television images in the comparator 22 can take place by linear comparison. If two lines do not coincide, then the crack has continued inside these lines. The output of the comparator is connected with a microprocessor 23 for operational control and data processing and the microprocessor output is connected to a data output unit 24. The microprocessor 23 contains a counter which counts those lines in which there is not coincidence between the two television images. The meter indication of this counter thus represents the crack development since the last measurement. The data output may take place by means of a pointer, the crack length, the number of load cycles, the crack velocity, the measuring instalment number, the clock time, etc. being indicated.

The microprocessor establishes, beyond that, whether the crack is approaching one of the edges of the television image, and controls in dependence thereon, the motor drive 28 for the position control of the television camera 17 with the front microscope attachment 16. A distance recorder 25 is coupled with the front microscope attachment 16 and determines distance of the front microscope attachment 16 from the test piece 11 and supplies this value to the motor drive 28. This actual value is compared with the desired value supplied from the microprocessor 23 and there is controlled as a function of the deviation, a sliding carriage on which is fixed the television camera 17 with the front microscope attachment and the distance recorder. The sliding carriage (not shown) can travel in three planes extending at right angles to one another.

The microprocessor 23 also controls the measuring cycle program control 15 and, beyond this, line and frame sync circuit 26 for the television camera 17 in such a way that the taking of a television image results only when the load rests for a short time on the test piece.

The timing of the line and frame sync circuit 26, of the measuring cycle program control 15, of the discriminator 18, of the store 21 and of the microprocessor 23 takes place through a sync generator 27. This may be a crystal-controlled oscillator.

We claim:

1. Crack development measuring equipment for use in conjunction with a loading device in which a test piece can be clamped, and having an optical measuring tool trained on the test piece, said equipment comprising:
   - a television camera cooperating with said optical measuring tool,
   - control means coupled to said television camera and to said loading device, for causing said loading device to load said test piece in periodic intervals, and for causing said television camera to produce a television image only between such intervals of loading,
   - a discriminator, connected to said camera, for converting the image elements of each television image into binary pulses,
   - a memory, connected to said discriminator, for temporarily storing the binary pulses of each television image, and
   - a digital comparator connected to said memory and to said discriminator to compare the contents of said memory with the binary pulses of a consecutive television image, the output of said comparator being indicative of the development of a crack in the test piece.

2. Crack development measuring equipment according to claim 1 wherein said comparator counts and indicates the number of non-coincident binary pulses of the compared television images.

3. Crack development measuring equipment according to claim 1 or 2 wherein said optical measuring tool includes a front microscope attachment connected to the television camera.

4. Crack development measuring equipment according to claim 1 wherein said television camera is mounted so that the line scanning direction is at right angles to the direction of said crack, and wherein said comparator compares said television images through linear comparison.

5. Crack development measuring equipment according to claim 1 or 4 wherein said television camera is mounted on a sliding carriage which can moved in three orthogonal planes under control of a positioning control signal.

6. Crack development measuring equipment according to claim 5 further comprising position control means for providing positioning control signals to said television camera carriage in response to the measured crack development indicated by the output of said comparator.

7. Crack development measuring equipment according to claim 1 wherein said discriminator further produces a reference grid parallel to the television image coordinates.

8. Crack development measuring equipment according to claim 1 further comprising a sync generator for timing the scan line and frame synchronization of the television camera and for timing the input and output of said memory and the operation of said comparator.

9. Apparatus for measuring the expansion of a crack in a test piece mounted in a loading device, comprising:
   a video camera mounted to view said test piece and to provide a video signal representing an image of said test piece including said crack,
   measuring cycle program control means coupled to said video camera and to said loading device, for directing said loading device to periodically subject said test piece to a load, and for causing said video camera to provide said video signal at times when no load is being provided by said loading device,
   a discriminator and digitization means, cooperating with said video camera, for digitizing each provided video signal,
   a digital image memory, connected to said discriminator and digitization means, for temporarily storing each digitized video signals, and
   digital comparator means, connected to said image memory and to said digitization means, for comparing each earlier stored video signal with a later provided digitized video signal from said discriminator and digitization means, the output of said comparator means being indicative of crack expansion in the test piece.

10. Apparatus according to claim 9 wherein said video camera is mounted with the line scan direction perpendicular to the principal direction of said crack, and wherein said comparator means counts the number of digitized elements per scan line which are different between said earlier stored video signal and said later provided video signal, the resultant count being indicative of crack expansion.

11. Apparatus according to claim 9 wherein said provided video signal is digitized by providing a binary signal of one value if the detected light intensity is above a threshold value and providing a binary signal of the opposite value if the video signal is below said threshold value.

12. Apparatus according to claim 11 wherein said comparator means counts the total number of non-coincident binary values in the compared video signals, said number being indicative of said crack expansion.

13. Apparatus according to claim 9 wherein said comparator means determines the number of lines in said later provided video signal in which a change in picture content has taken place as compared with said earlier stored video signal.

14. Apparatus according to claim 9 further comprising: motor drive positioning control means, controlled in response to the output of said comparator means, for repositioning said video camera in the event that said crack expands to near the edge of the field of view of said video camera.

15. A method for measuring the development of a crack in a test piece mounted in a loading device, comprising the steps of:
   (a) storing a digitized video image of the test piece in a storage device,
   (b) digitally comparing the contents of the storage device with a next digitized video image of the test piece taken subsequent to the first video image,
   (c) counting the number of picture elements of said next video image in which a change in picture content has taken place as compared with said stored video image, said number of elements being indicative of the extent of crack development in the test piece,
   (d) storing said next digitized image in the storage device, and
   (e) repeating steps (b), (c), and (d) above.

16. A method for measuring the development of crack in a test piece mounted in a loading device, the method comprising:
   (a) storing one digitized video image of the test piece in a storage device,
   (b) obtaining a next digitized video image of the test piece taken subsequent to loading of the test piece by the loading device, and
   (c) digitally comparing the number of video image elements in said next video image in which the crack appears with the number of image elements in said one video image in which the crack appears, the difference in number of such image elements being indicative of the extent of crack development as a result of the loading applied by said device between acquisition of said one and next images.

17. A method for measuring the development of crack in a test piece mounted in a loading device, the method comprising:
   (a) storing one digitized video image of the test piece in a storage device,
   (b) obtaining a next digitized video image of the test piece taken subsequent to loading of the test piece by the loading device, the video scan lines of said one and next video images being at an angle to the principal direction of crack development, and
   (c) digitally comparing the number of video scan lines in said next video image in which the crack appears with the number of lines in said one video image in which the crack appears, the difference in number of such lines being indicative of the extent of crack development as a result of the loading applied by said device between acquisition of said one and next images.

* * * * *